(12) United States Patent
Huang et al.

(10) Patent No.: US 10,510,445 B2
(45) Date of Patent: Dec. 17, 2019

(54) METHODS AND SYSTEMS FOR DISPLAYING CLINICAL PARAMETERS

(71) Applicant: SHENZHEN MINDRAY BIO-MEDICAL ELECTRONICS CO., LTD., Shenzhen (CN)

(72) Inventors: Chenghua Huang, Shenzhen (CN); Xiaocheng Tang, Shenzhen (CN); Ruiling Pan, Shenzhen (CN); Lei Qing, Shenzhen (CN); Xinsheng Li, Shenzhen (CN); Jie Qin, Shenzhen (CN); Jianfeng Jiang, Shenzhen (CN)

(73) Assignee: Shenzhen Mindray Bio-Medical Electronics Co., Ltd.

( * ) Notice: Subject to any disclaimer, the term of this patent is extended or adjusted under 35 U.S.C. 154(b) by 0 days.

(21) Appl. No.: 15/396,050

(22) Filed: Dec. 30, 2016

(65) Prior Publication Data
US 2017/0124273 A1 May 4, 2017

Related U.S. Application Data

(63) Continuation-in-part of application No. PCT/CN2015/088042, filed on Aug. 25, 2015, and a continuation-in-part of application No. PCT/CN2014/081296, filed on Jun. 30, 2014.

(51) Int. Cl.
| | |
|---|---|
| *G16H 40/63* | (2018.01) |
| *A61B 5/00* | (2006.01) |
| *G06T 11/20* | (2006.01) |
| *G06T 11/00* | (2006.01) |

(52) U.S. Cl.
CPC ............ *G16H 40/63* (2018.01); *A61B 5/4821* (2013.01); *G06T 11/206* (2013.01); *A61B 5/7445* (2013.01); *G06T 11/001* (2013.01); *G06T 2210/41* (2013.01)

(58) Field of Classification Search
CPC .... G06F 19/3406; A61B 5/4821; G16H 40/63
USPC ......................................................... 345/440
See application file for complete search history.

(56) References Cited

U.S. PATENT DOCUMENTS

| | | | | |
|---|---|---|---|---|
| 2006/0217628 | A1* | 9/2006 | Huiku ...................... | A61B 5/02 600/544 |
| 2006/0241359 | A1 | 10/2006 | Nagai et al. | |
| 2007/0052703 | A1* | 3/2007 | Seto .......................... | G06T 1/60 345/419 |
| 2007/0106183 | A1* | 5/2007 | Suzuki ................. | A61B 5/02438 600/595 |
| 2009/0024006 | A1* | 1/2009 | Bessette ................... | A61B 5/00 600/301 |

(Continued)

FOREIGN PATENT DOCUMENTS

| | | |
|---|---|---|
| CN | 1470216 A | 1/2004 |
| CN | 2620531 Y | 6/2004 |

(Continued)

*Primary Examiner* — Hai Tao Sun
(74) *Attorney, Agent, or Firm* — Kory D. Chirstensen

(57) ABSTRACT

Methods and systems are disclosed for displaying clinical parameters in a chart that can be easily interpreted by medical personnel. A system includes a parameter acquiring device configured to acquire data signals indicative of depth of anesthesia in real time. The system also includes a data processor and a display device, which are in communication with the parameter acquiring device.

15 Claims, 15 Drawing Sheets

(56) References Cited

U.S. PATENT DOCUMENTS

| | | | |
|---|---|---|---|
| 2009/0149724 A1* | 6/2009 | Mark | A61B 5/0205 600/301 |
| 2010/0081942 A1* | 4/2010 | Huiku | A61B 5/02028 600/483 |
| 2015/0253163 A1 | 9/2015 | Cortez | |

FOREIGN PATENT DOCUMENTS

| | | |
|---|---|---|
| CN | 1879564 A | 12/2006 |
| CN | 101231676 A | 7/2008 |
| CN | 101843524 A | 9/2010 |
| CN | 102422290 A | 4/2012 |
| CN | 202288276 U | 7/2012 |
| CN | 103040460 A | 4/2013 |
| CN | 203263388 U | 11/2013 |
| CN | 103876835 A | 6/2014 |
| JP | 2004180919 | 7/2004 |
| JP | 2004180939 A | 7/2004 |
| JP | 2009022671 A | 2/2009 |
| WO | 2015100347 A2 | 7/2015 |

\* cited by examiner

METHODS AND SYSTEMS FOR DISPLAYING CLINICAL PARAMETERS

TECHNICAL FIELD

This disclosure relates generally to medical systems and more particularly to systems and method for displaying clinical parameters.

BACKGROUND OF THE INVENTION

Various medical devices, including patient monitors, analyze and display different kinds of physiological and/or psychological parameters detected by one or more sensors connected to a patient. These parameters may be shown in waveform or numerical form, wherein the waveform could depict values of the parameters for a period and the numerical form could depict current values of the parameters. Medical staff can monitor the patient's physical conditions by the medical device, and further identify alarming conditions by detected parameter values.

For example, for a patient in surgery or under anesthesia, a multi-parameter patient monitor may be used to monitor conventional physiological parameters of the patient, such as blood pressure, heart rate, and blood oxygen, and display information of detected parameters, such as by waveform, numerical values, or otherwise, in an interface of the patient monitor. A single parameter monitor for Bispectral Index (BIS) monitoring and another single parameter monitor for Neuromuscular Transmission (NMT) monitoring may be used to monitor and display conditions of awareness and muscle relaxation. In order to ascertain the depth of anesthesia for the patient, medical staff have to view information on these monitors and then make a judgment based on experience. Because the amount of information on these monitors is vast, doctors have to spend time choosing parameters that may be used to determine the depth of anesthesia. On another hand, because all useful information is scattered on different monitors, the doctor has to view all parameters one by one and then combine the current and past parameters to make the judgment. In addition, patient monitors may be provided by different manufactures, so the parameters displayed on each patient monitor may be inconsistent. These situations affect the medical staff judgment regarding whether a dose of anesthetic is suitable and impact the doctor's ability to effectively make medical judgments.

SUMMARY

A system and method for displaying clinical parameters is disclosed. The aforementioned may be achieved by providing: a method for displaying clinical parameters, comprising detecting values of the at least three clinical parameters at the same time; comparing the detected values of the at least three clinical parameters with preset threshold ranges, wherein each threshold range corresponds to one clinical parameters; generating a spider chart wherein each spoke of the spider chart represents one clinical parameter, and each spoke is divided into three sections specifying whether detected values fall within, above, or below the corresponding threshold ranges. The aforementioned may also be achieved by providing: a system comprising a parameter acquiring device configured to receive at least three clinical parameters of a patient at a particular time; and a processing unit configured to display on a display device a spider chart comprising a plurality of radial spokes, each spoke representing a range of values for one clinical parameter and indicating a point corresponding to a detected value of the clinical parameter. The aforementioned may also be achieved by providing: a method comprising detecting via a plurality of sensors values of at least three clinical parameters of a patient at a particular time; and displaying on a display device a spider chart comprising a plurality of radial spokes, each spoke representing a range of values for one clinical parameter and indicating a point corresponding to a detected value of the clinical parameter. The aforementioned may also be achieved by providing: a system for graphically representing a depth of anesthesia for a patient, comprising a parameter acquiring device configured to detect, via a plurality of sensors, at least two sets of clinical parameters for the patient at a particular time; and a processing device configured to display graphical representations of the at least two sets of clinical parameters in at least two respective areas of a display device, wherein the at least two sets of clinical parameters are selected from group consisting of muscle relaxation, awareness, and pain strength. The aforementioned may also be achieved by providing: a method for graphically representing a depth of anesthesia for a patient, comprising detecting, via a plurality of sensors, at least two sets of clinical parameters for the patient at a particular time; and displaying graphical representations of the at least two sets of clinical parameters in at least two respective areas of a display device, wherein the at least two sets of clinical parameters are selected from group consisting of muscle relaxation, awareness, and pain strength.

DETAILED DESCRIPTION

The following description provides embodiments with specific details to one skilled in the art for a better understanding of the present disclosure. However, it should be understood that the present disclosure may be practiced even without these details. In some embodiments, to avoid unnecessarily obscuring the following description, well-known structures and functions are not illustrated or described in detail. In the specification and claims of the present disclosure, terms such as "including" and "comprising" should be comprehended as an inclusive meaning instead of an exclusive or exhaustive meaning, i.e., it means "including but not limited to" unless specifically described otherwise in the context. In this detailed description section, singular or plural terms include both the plural and singular meanings as well.

Figure 1:
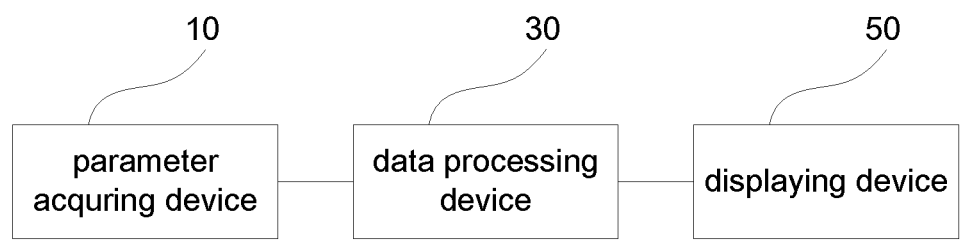
FIG. 1 is a schematic diagram of a patient monitoring system according to an embodiment.

As shown in FIG. 1, a patient monitoring system includes a parameter acquiring device 10, a data processor 30, and a display device 50 in successive communication. A person of skill in the art will recognize that the patient monitoring system could include or be comprised of a variety of medical devices or systems, such as anesthesiology systems. Each component will be described in detail below.

The parameter acquiring device 10 acquires data signals indicative of the depth (sometimes variously referred to as the "adequacy") of anesthesia in real time. Awareness, pain strength, and muscle relaxation are three important dimensions of information used to decide the depth of anesthesia. In one embodiment, awareness and muscle relaxation may be reflected by values of BIS and NMT respectively; the pain strength could not be reflected directly by a single value of a monitoring parameter, but the pain strength may be reflected by changes in blood pressure, heart rate, or hormone level. Other than awareness, pain strength, and muscle relaxation, the depth of anesthesia may be decided by other information including two or more than three dimensions, and parameters used to reflect the dimensions may be selected according to need.

The data processor 30, such as a CPU, may process the data signals acquired by the parameter acquiring device 10 and generate visualization representation data. The visualization representation data could include multiple dimensions of information used to indicate the depth of anesthesia, and each dimension of information may be reflected by at least one parameter which could characterize the depth of anesthesia. For example, awareness, pain strength, and muscle relaxation are three dimensions of information acquired by data signal, and the visualization representation data includes the three dimensions of information that are awareness, pain strength, and muscle relaxation. Awareness and muscle relaxation may be reflected by BIS and NMT, and muscle relaxation may be reflected by at least one parameter selected from changes in blood pressure, heart rate, or hormone level. The medical staff could select a number and/or types of parameters which could characterize pain strength; a number and/or types of parameters which could reflect awareness and muscle relaxation may be preset or selected by a user.

Figure 3:
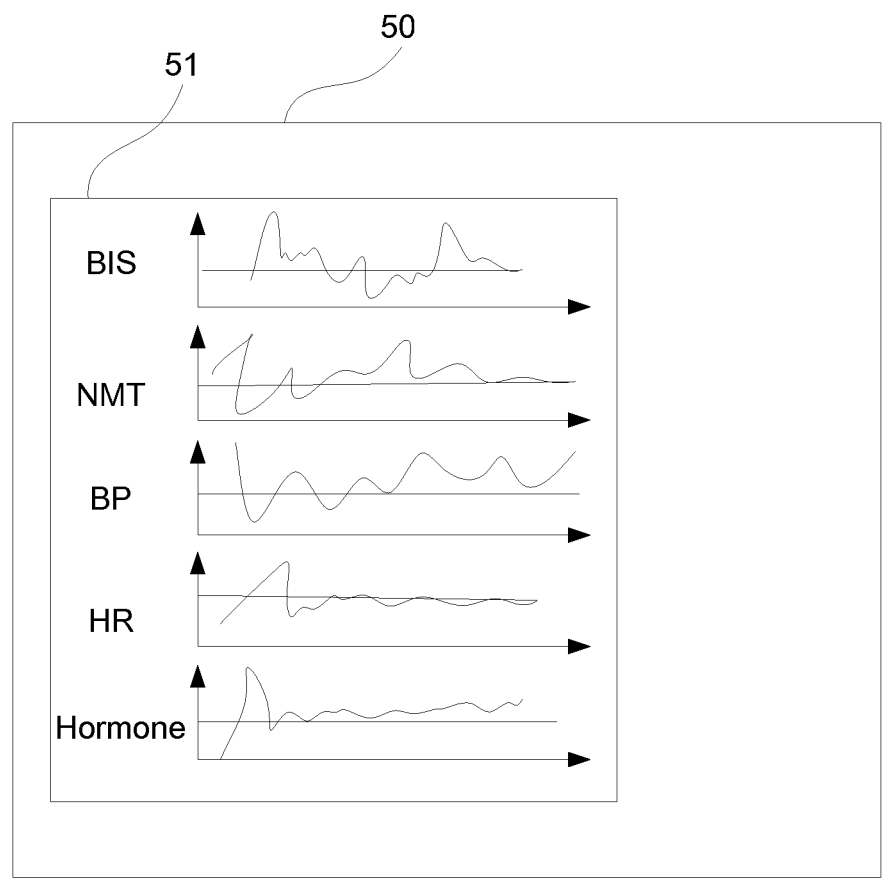
FIG. 3 is a schematic diagram displaying part of a user interface provided by the display device according to an embodiment.

The display device 50, such as a computer monitor, could display the visualization representation data generated by the data processor 30 in an anesthesia depth displaying area 51. The visualization representation data may include multiple dimensions of information used to indicate the depth of anesthesia, and each dimension of information may be reflected by a corresponding parameter. For example, awareness, pain strength, and muscle relaxation are three dimensions of information used; awareness and muscle relaxation may be reflected by BIS and NMT, and muscle relaxation may be reflected by changes in blood pressure, heart rate, or hormone level. The display device 50 displays these parameters in the anesthesia depth displaying area 51, as shown in FIG. 3 (this two-dimensional coordinate is just a schematic diagram displaying each dimension of information), and the medical staff could determine whether the anesthetic is adequate based on the displayed information. The display device 50 may be a touch screen or non-touch screen. For example, the display device 50 may be a screen of a patient monitor.

Figure 2:
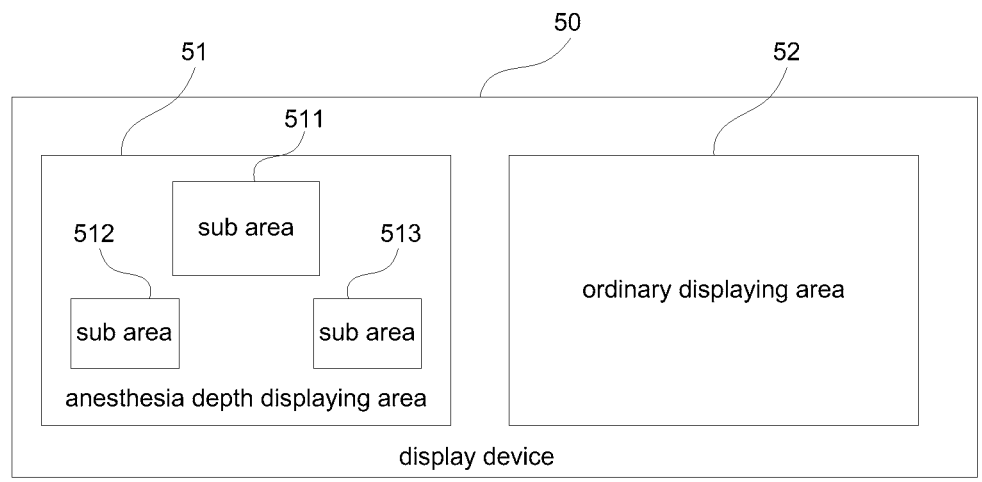
FIG. 2 is a schematic diagram of a display device of the patient monitoring system according to an embodiment.

Except for at least one anesthesia depth displaying area 51, an ordinary displaying area 52 for displaying information of conventional or other physiological parameters, such as pulse rate, temperature, respiratory rate, venous oxygen saturation, and hemodynamics, could also be included. The anesthesia depth displaying area 51 and ordinary displaying area 52 are independent from each other. As shown in FIG. 2, the ordinary displaying area 52 may be divided into a plurality of sub displaying areas juxtaposed in a horizontal direction, and each sub displaying area may display information of one parameter. In a specific embodiment, the anesthesia depth displaying area 51 may be located at the lower left corner or center of the patient monitor screen. In some cases, the anesthesia depth displaying area 51 and ordinary displaying area 52 do not overlap each other; in some cases, the anesthesia depth displaying area 51 could cover a part of the ordinary displaying area 52. In a case, the whole screen of the patient monitor may be viewed as the ordinary displaying area 52; in other cases, the anesthesia depth displaying area 51 could cover the whole screen of the patient monitor, or may be located at another screen of a networked or associated patient monitor/patient monitoring system. By displaying parameter information of each dimension used to indicate the depth of anesthesia in the anesthesia depth displaying area 51, the medical staff could check the parameter information of each dimension and then quickly make a decision of what to do next.

In one embodiment, by displaying the parameter information of three dimensions, which are awareness, pain strength, and muscle relaxation, in real time, a comprehensive organization and presentation of the depth of anesthesia are provided by multiple dimensions, which could help the medical staff to decide the depth of anesthesia.

In one embodiment, the parameter acquiring device 10, data processor 30, and display device 50 included in the patient monitoring system are three components divided by functions. Therefore, the number of components or how the functionality is implemented may be set according to specific circumstances. For example, the parameter acquiring device 10 may be a parameter module of a plugin monitor or a parameter board in a non-plugin monitor, and the data processor 30 may be a main control unit of the plugin monitor or a host of the non-plugin monitor. The parameter acquiring device 10 may be an interface of the main control unit, and the parameter acquiring device 10 acquires data signals from sensors, other monitors, or networks; the parameter acquiring device 10 may be a sensor for acquiring original data signals, and the data processor 30 including one or more sub devices could process the original data signals and generate the visualization representation data.

As shown in FIGS. 1 and 2, the patient monitoring system in one embodiment includes the parameter acquiring device 10, the data processor 30, and the display device 50 connected successively. How the display device 50 displays the multiple dimensions of information for indicating the depth of anesthesia is specifically described below, and a corresponding method of displaying patient parameters is described.

In one embodiment, each anesthesia depth displaying area 51 may include multiple sub areas, the number of the sub areas is equal to the number of the dimensions, and each sub area corresponding to a dimension may display information of the dimension. For example, awareness, pain strength, and muscle relaxation are three dimensions of information used, and the three dimensions of information are displayed on the anesthesia depth displaying area 51. As shown in FIG. 2, the anesthesia depth displaying area 51 may be divided into three sub areas 511, 512, and 513. The three sub areas 511, 512, and 513 may display awareness, pain strength, and muscle relaxation respectively, and each dimension of information may be reflected by at least one parameter, such that awareness and muscle relaxation may be reflected by BIS and NMT, and muscle relaxation may be reflected by changes in blood pressure and heart rate. In one embodiment, the depth of anesthesia may be indicated by physiological parameters and/or psychological parameters.

The parameter information of each sub area may include a parameter name, a current monitoring value, a value change trend, and a status indicator, or any combination thereof. The parameter information could include the parameter name and current monitoring value; the parameter name and value change trend; the parameter name and status indicator; the parameter name, current monitoring value, and value change trend; or the parameter name, current monitoring value, value change trend, and status indicator. The status indicator could indicate whether the current monitoring value falls within a preset threshold of a corresponding parameter. The preset threshold may be set based on experience, and the preset threshold may be based on a system default set or a user set obtained from a human-computer interaction interface. The parameter name (if displayed) may be shown as text in various languages, or displayed as icons or diagrams.

In one embodiment, the information of each dimension may be displayed in text format on the corresponding sub area. For example, BIS information, which may include the current monitoring BIS value and BIS status indicator, may be displayed in text on the sub area 511. Other sub areas are similar.

In another embodiment, the information of each dimension may be displayed in graphic format on the corresponding sub area. For example, BIS information may be displayed in graphic format on the sub area 511. A diagram, such as a histogram, may be used to represent the monitored BIS value, and whether the monitored BIS value is within a normal range may be represented by a color of the histogram. Other sub areas are similar.

In this specification, the graphic format may include at least one of a graphic and a combination of a graphic and color or a pattern. That is, the graphic format may be a combination of a graphic and color, a combination of a graphic and a pattern, or a combination of a graphic, color, and a pattern. The graphic may be one of or any combination of a line, a rectangular bar, a pie chart, a meter chart, and a two-dimensional graph.

Figure 4:
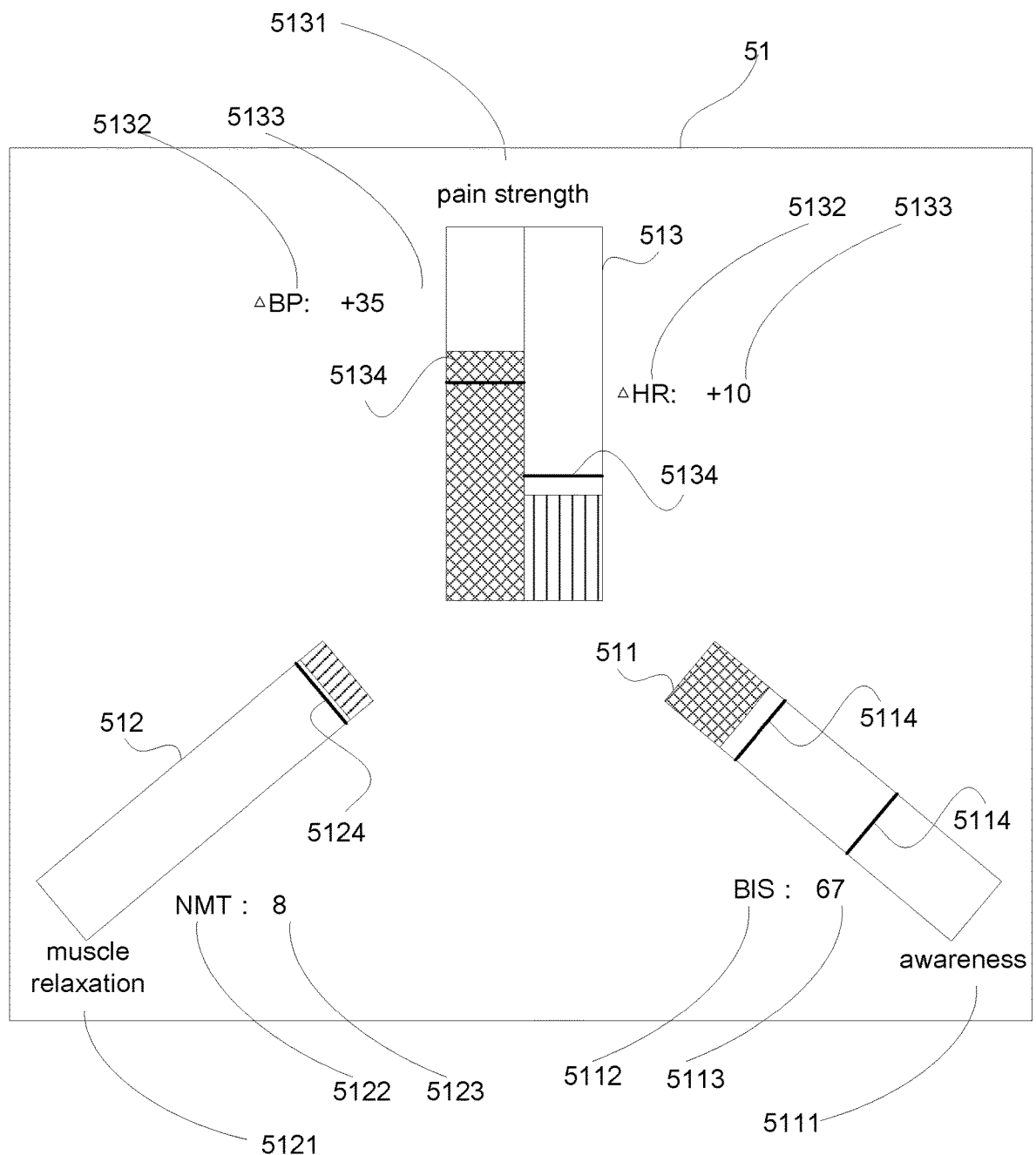
FIG. 4 is a schematic diagram displaying depth of anesthesia according to an embodiment.
Figure 5:
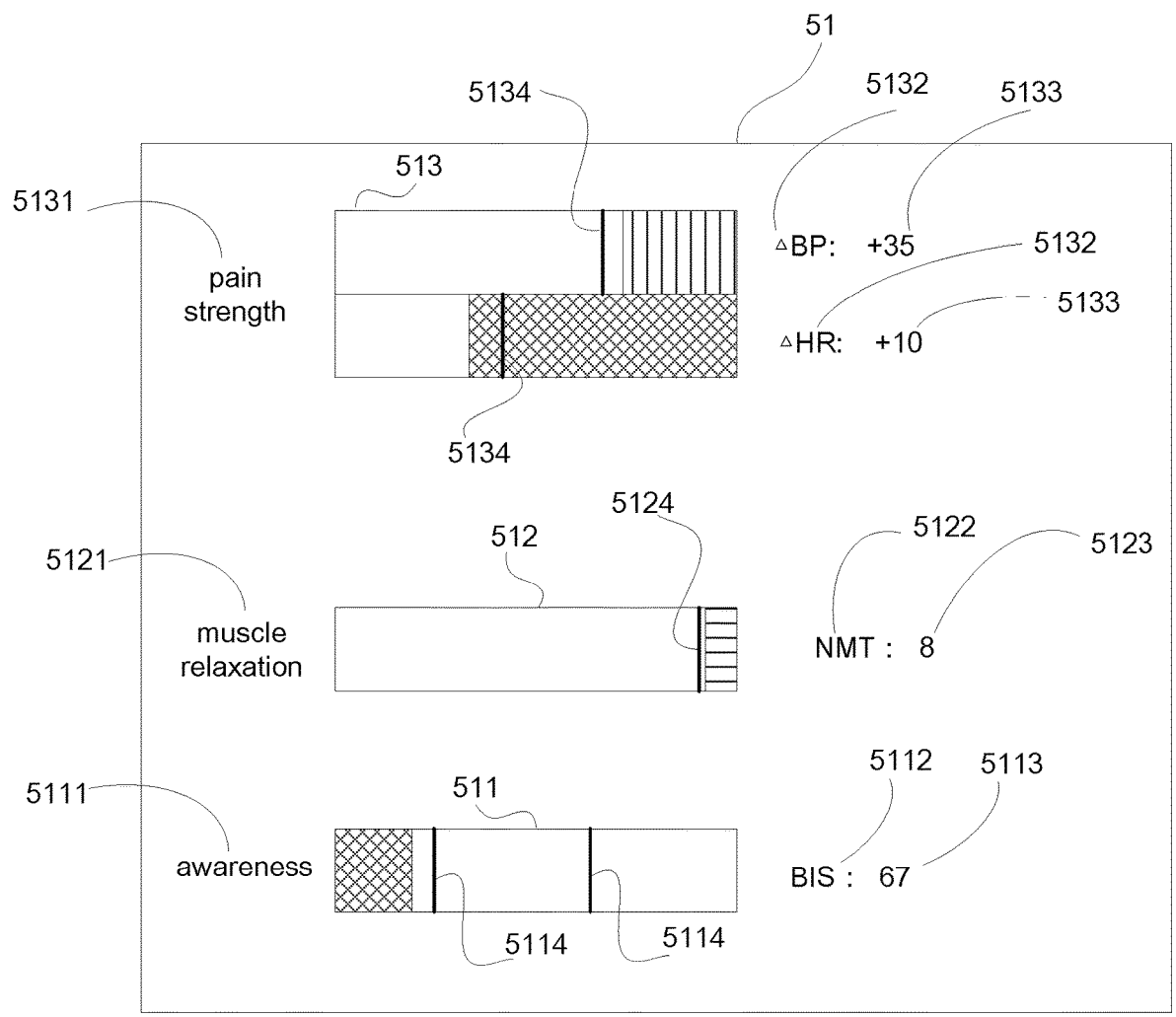
FIG. 5 is a schematic diagram displaying the depth of anesthesia according to another embodiment.

In the embodiment, the information of each dimension may be displayed in a text and graphic format, and the information for each sub area is presented in the same way. For example, as shown in FIG. 4, the information of the awareness dimension is displayed on the sub area 511. The name of the dimension (awareness) 5111, the name of the parameter (BIS) 5112 used in the dimension, and the current monitoring value (67) 5113 are displayed in text, and a rectangular bar may be used to represent the BIS. A preset threshold of BIS may be displayed by two lines 5114 in the rectangular bar, the current BIS value is represented by a length of a part of the rectangular bar with a pattern, and a BIS status may be indicated by the pattern such that if the current BIS value falls within the preset threshold of BIS, a part of the rectangular bar with a length proportional to the BIS value is a painted stripe. If the current BIS value does not fall within the preset threshold of BIS, a part of the rectangular bar with a length proportional to the BIS value is painted plaid. The information of muscle relaxation is displayed on the sub area 512. The name of the dimension (muscle relaxation) 5121, the name of the parameter (NMT) 5122 used in the dimension, and the current monitoring value (8) 5123 are displayed in text, and a rectangular bar may be used to represent muscle relaxation. A preset threshold value of NMT may be displayed by a line 5124 in the rectangular bar, the current NMT value is represented by a length of a part of the rectangular bar with a pattern, and a NMT status may be indicated by the pattern such that if the current NMT value is smaller than the preset threshold of NMT, a part of the rectangular bar with a length proportional to the NMT value is painted plaid; if the current NMT value is greater than the preset threshold of NMT, a part of the rectangular bar with length proportional to the NMT value is painted stripe. The information of pain strength is displayed on the sub area 513. The name of the dimension (pain strength) 5131, the name of the parameters (changes of blood pressure and heart rate, ΔBP and ΔHR) 5132 used in the dimension, and the current changes of blood pressure and heart rate (+35, +10) 5133 are displayed in text, and two rectangular bars may be used to represent the two parameters respectively. Preset thresholds of ΔBP and ΔHR may be displayed respectively by lines 5134 in the rectangular bars. For each parameter, the current value is represented by a length of a part of the rectangular bar with a pattern, and the corresponding parameter status may be indicated by the pattern such that if the current ΔBP is smaller than the preset threshold of ΔBP, a part of the rectangular bar with a length proportional to the ΔBP value is painted plaid; if the current ΔBP value is greater than the preset threshold of A BP, a part of the rectangular bar with length proportional to the ΔBP value is painted stripe. If the current ΔHR is smaller than the preset threshold of ΔHR, a part of the rectangular bar with a length proportional to the ΔHR value is painted plaid; if the current ΔHR value is greater than the preset threshold of ΔHR, a part of the rectangular bar with a length proportional to the ΔHR value is painted stripe. One skilled in the art knows current values of parameters, parameter thresholds, and parameter statuses may be represented by other ways; for example, a current value of a parameter may be indicated by a mark, such as a triangle or an arrow. As shown in FIG. 4, a spider chart is formed by the three sub areas 511, 512, and 513. In other embodiments, the three rectangular bars may be juxtaposed (as shown in FIG. 5) or placed side by side vertically, or the three rectangular bars could constitute a triangle.

Figure 6:
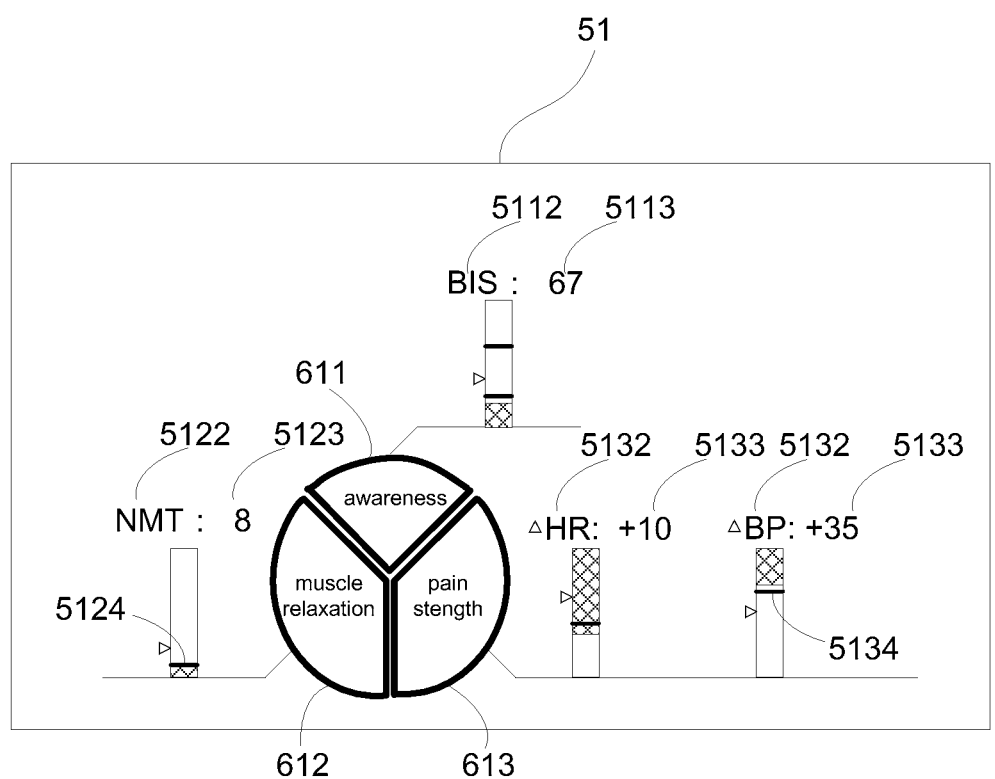
FIG. 6 is a schematic diagram displaying the depth of anesthesia according to another embodiment.
Figure 7:
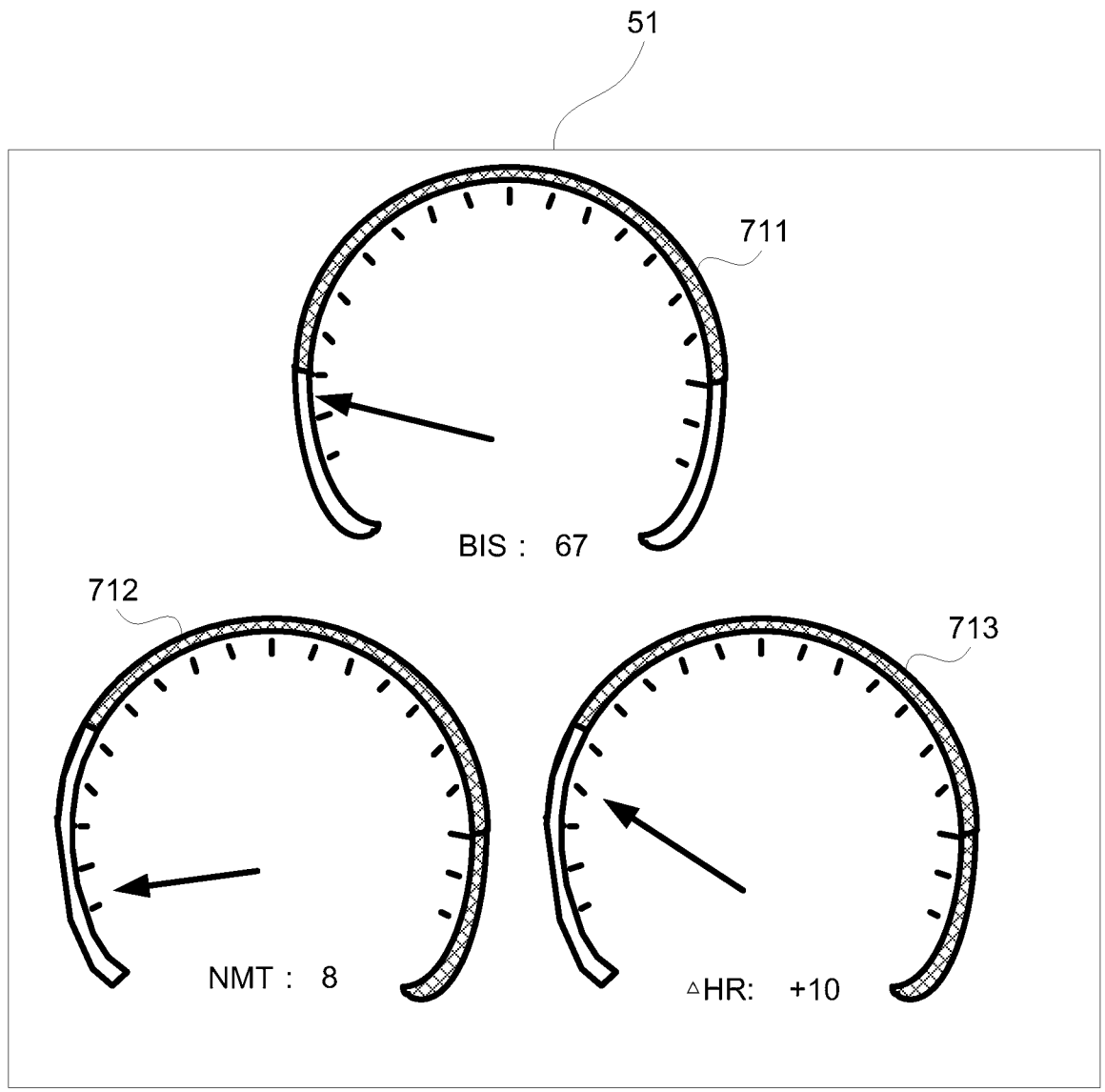
FIG. 7 is a schematic diagram displaying the depth of anesthesia according to another embodiment.

Other than rectangular bars, the dimensions may be represented by other shapes or charts, such as sectors 611-613 (as shown in FIG. 6) or meter charts 711-713 (as shown in FIG. 7). In addition, the information of each dimension may be represented by a rectangular bar and a two-dimensional coordinate. One skilled in the art could know how to present a parameter trend in a two-dimensional coordinate or tabulation, as the way of presenting ECG in a patient monitor. As shown in FIG. 6, the name of each dimension is shown in each sector, and the corresponding parameter information is shown by each rectangular bar. In addition, the value of each parameter may be represented by the area size of the corresponding sector, and the corresponding threshold line may be shown in the sector.

In one embodiment, as shown in FIG. 7, the parameter information may be represented by a meter chart. The current value of the parameter may be indicated by a pointer and displayed in text; the threshold range of the parameter may be indicated by a part of the outer ring painted with a pattern such that for each meter chart, the part of the outer ring corresponding to the threshold range is painted plaid. How to place the meter charts may be changed according to the number of the dimensions.

In some embodiments, more than two parameters may be used to reflect pain strength, and then more rectangular bars may be used in the pain strength dimension. The rectangular bars may be juxtaposed, be placed side by side vertically, distributed symmetrically around a center point, and so on.

In one embodiment, in order to indicate the depth of anesthesia, dimensions, such as awareness, muscle relaxation, and pain strength, and the corresponding parameter information are displayed in graphic format. On one side, the depth of anesthesia is depicted by three dimensions, with each dimension corresponding to a sub area, and the parameter information used to reflect the corresponding dimension is displayed in the corresponding sub area. The number of dimensions, names, and parameters corresponding to each dimension may be determined by the medical staff (as described in embodiment three). On another side, the parameter information used is displayed in graphic format; for example, the current value of the parameter is represented by the height of a corresponding rectangular bar, and whether the parameter is in normal status or abnormal status may be represented by the color of the pattern of the rectangular bar. The medical staff could get general information and specific information at a glance, and the medical staff does not need to look for a variety of related information from the whole screen to find out the depth of anesthesia. So the convenience and maneuverability of the monitoring system may be improved to a certain extent. In one embodiment, whether the parameter is in normal or abnormal status may be distinguished by the pattern or color used to paint the rectangular bar. In addition, the threshold value of each parameter may be set by the medical staff or by a default value (an experience value). The name of each dimension may be displayed by text, symbol, schematic, a thumbnail, and so on. The name of each dimension may be displayed in the corresponding sub area or a concentrated information area.

Figure 8:
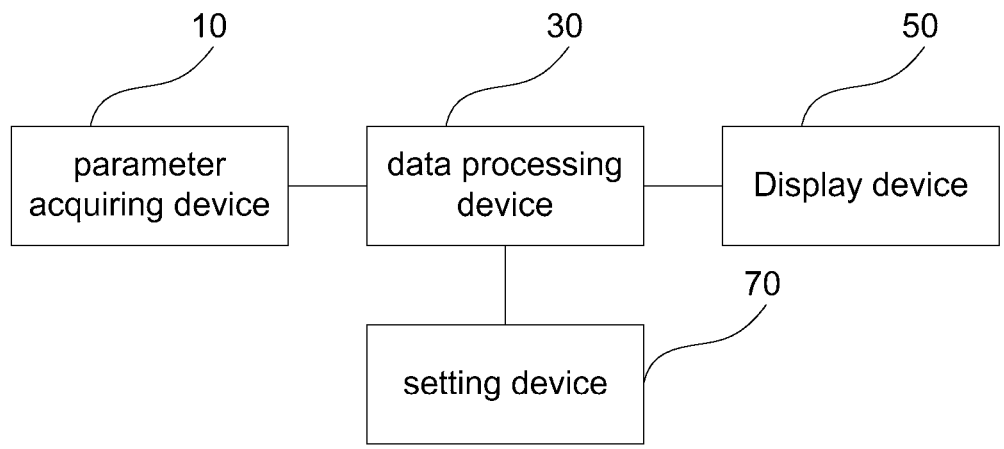
FIG. 8 is a schematic diagram of the patient monitoring system according to another embodiment.

As shown in FIG. 8, except for the parameter acquiring device 10, the data processor 30, and the display device 50, a patient monitoring system may also include a setting device 70 connecting to the data processor 30. The setting device 70 could set information to be displayed automatically or by user input. The information to be displayed may include information of multiple dimensions for reflecting the depth of anesthesia, the name of each dimension, the number of parameters for indicating each dimension, and information of each parameter. The dimensions for reflecting the depth of anesthesia and the parameter for indicating each dimension may be preset in the patient monitoring system. In an automatic setting mode, the dimensions used and the parameters used for each dimension may be automatically set by parameters monitored by the patient monitoring system. In a user setting mode, the dimensions used and the parameters used for each dimension may be set according to user input. In other words, the medical staff could decide the dimensions and parameters used to reflect the depth of anesthesia.

Figure 9:
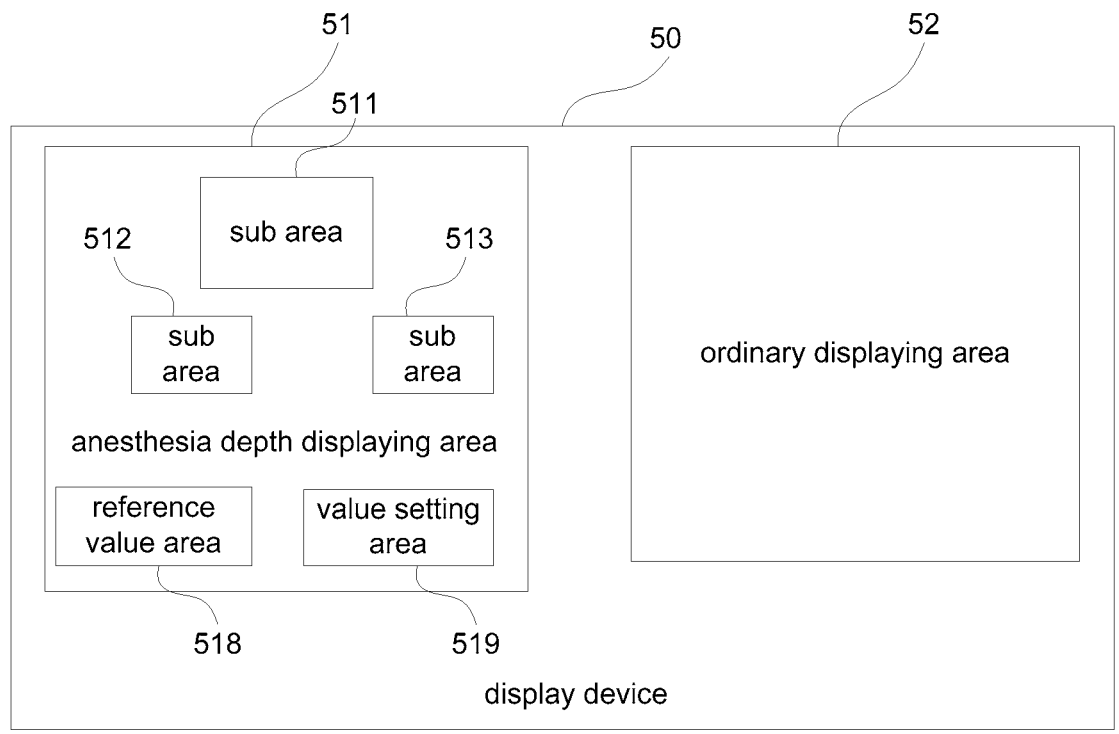
FIG. 9 is a schematic diagram of a display device of the patient monitoring system according to another embodiment.

The above-described patient monitoring systems may include the setting device that could set the information to be displayed automatically, such that awareness, muscle relaxation, and pain strength are the three dimensions used. In one embodiment, the setting device 70 could set information to be displayed by user input according to needs. One skilled in the art could know that the patient monitoring system could provide a human-computer interaction interface for the medical staff. As shown in FIG. 9, a value setting area 519 within the anesthesia depth displaying area 51 may be provided by the display device 50, and the information to be displayed may be set by the medical staff in the value setting area 519. One skilled in the art could know how to implement the value setting area 519 and establish the association between the value setting area 519 and the setting device 70.

In one embodiment, the setting device 70 may set a length of time involved in the parameter trend. The length of time could change automatically according to system time or be set by the medical staff.

In yet another embodiment, a patient monitoring system could also indicate baseline levels of vital sign parameters before anesthesia. As shown in FIG. 9, the anesthesia depth displaying area 51 may further include a reference value area 518. The baseline levels of vital sign parameters may be displayed in the reference value area 518. The baseline levels of vital sign parameters may be set by the following method:

a) the baseline levels of vital sign parameters may be set according to average values of the vital sign parameters during a period of time after the system starts running;

b) the baseline levels of vital sign parameters may be set according to values of the vital sign parameters at specific times decided by the medical staff; or c) the baseline levels of vital sign parameters may be set by the medical staff.

In one embodiment, the baseline levels of vital sign parameters before anesthesia and the trend of parameters related to the depth of anesthesia are displayed in graphic format, so the medical staff could easily determine whether the trend of parameters and the depth of anesthesia are appropriate. In one embodiment, the baseline levels of vital sign parameters before anesthesia may be replaced by vital sign parameters during anesthesia, or both the baseline levels of vital sign parameters before anesthesia and the vital sign parameters during anesthesia are used.

In each of the aforementioned embodiments, indicating the depth of anesthesia by multiple dimensions, such as awareness, pain strength and muscle relaxation, may be applied to various monitoring equipment, such as an anesthesia machine or respirator with a monitoring function. For each dimension, one or more parameters may be used. For example, no parameter could indicate pain strength directly, but changes of at least two parameters, such as changes of HR and BP, could indicate pain strength. In order to visually indicate the depth of anesthesia, current values of parameters, parameter thresholds, and parameter statuses may be represented in the anesthesia depth displaying area 51. By displaying the parameter information of each dimension used to indicate the depth of anesthesia in the anesthesia depth displaying area 51, the medical staff could check the parameter information of each dimension and then quickly make a decision of what to do next.

In addition, one skilled in the art could know how to display the information of each dimension and the parameter information of each dimension may be changed. For example, the parameter information, including current parameter value and threshold line, may be displayed only in abnormal status, detailed information of only one dimension and part of information for other dimensions are displayed, and so on.

Figure 10:
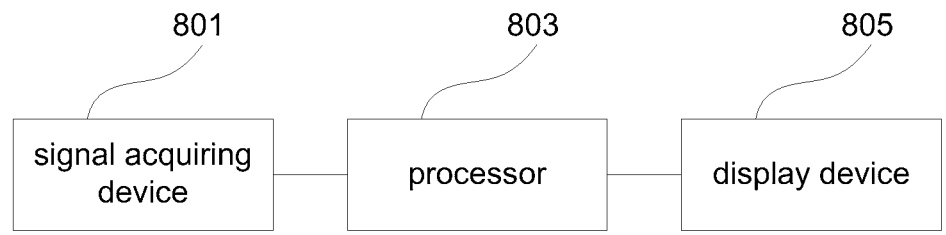
FIG. 10 is a schematic diagram of the patient monitoring system according to another embodiment.
Figure 11:
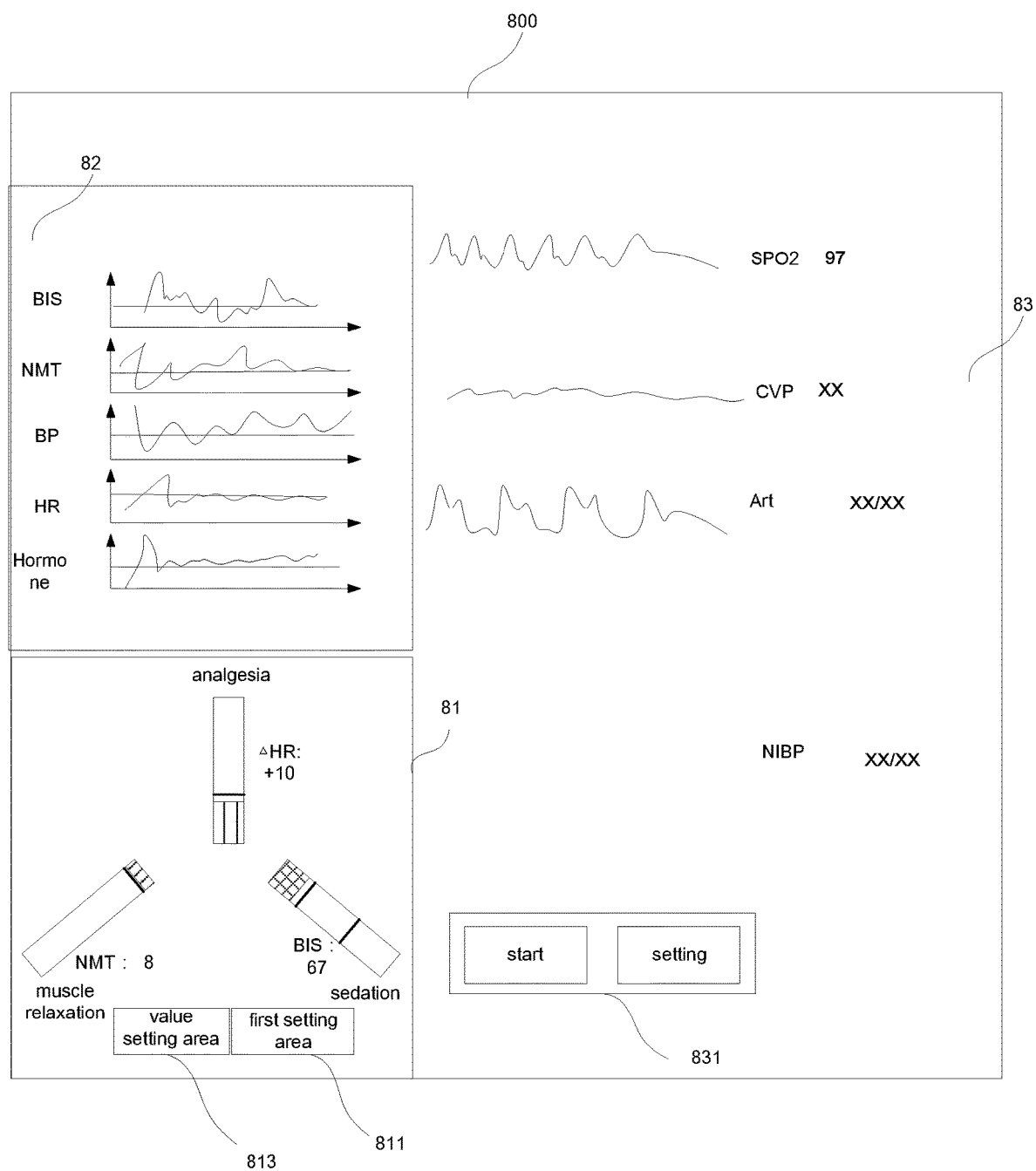
FIG. 11 is a flowchart illustrating a method of displaying patient parameters according to another embodiment.

As shown in FIG. 10, a patient monitoring system may include a signal acquiring device 801, a processor 803, and a display device 805. The signal acquiring device 801 may be connected to a patient and acquire parameter signals; the processor 803, connected with the signal acquiring device 801, may process the parameter signals received from the signal acquiring device 801 and generate visualization parameter information; the display device 805, including a displaying area, could display the visualization parameter information in a display interface 800 as shown in FIG. 11.

The display interface 800 may include an anesthesia depth displaying area 81, a short trend displaying area 82, and a general parameter displaying area 83. The anesthesia depth displaying area 81 may account for one-ninth to one-third, or one-tenth to one-half of the display interface 800. The anesthesia depth displaying area 81 may be located at the lower left corner, lower right corner, upper left corner, upper right corner, or center of the display interface 800. In some embodiments, the short trend displaying area 82 and anesthesia depth displaying area 81 may be called an anesthesia information displaying area. In some embodiments or conditions, part of all of the general parameter displaying area 83 may be overlapped by the anesthesia depth displaying area 81.

General parameters, such as Non-Invasive Blood Pressure (NIBP), Saturation of Peripheral Oxygen ($SpO_2$) and Central Venous Pressure (CVP), are displayed in the general parameter displaying area 83. In this disclosure, the general parameters may include parameters monitored in special situations, and anesthesia-related parameters are not excluded. The general parameter displaying area 83 may display waveforms and values of each general parameter using known techniques. That means each general parameter representing a single sign status or change of physiological status may be displayed in the general parameter displaying area 83 side by side.

Short trends of anesthesia-related parameters, such as 5- or 10-second short trends of BIS, NMT, BP, HR, and hormone, are displayed in the short trend displaying area 82. Reference values of the anesthesia-related parameters could also be displayed in the short trend displaying area 82. A reference value of an anesthesia-related parameter may be a mean value of the anesthesia-related parameter during a preset period before and/or after anesthesia, or a value inputted by the medical staff. In a specific embodiment, the anesthesia depth displaying area 81 could also include a reference value setting area 813. The reference value setting area 813 may be an operation button. If the medical staff presses the operation button, parameter values measured on that day may be set as the reference value of the corresponding parameter. A set of stored values measured earlier could also be set as the reference value of the corresponding parameter. Trends of each general parameter displayed in the general parameter displaying area 83 may be stored in the patient monitoring system, and the trends of each general parameter may be viewed by specialized trend viewing pages.

The visualization parameter information related to the depth of anesthesia may be displayed in the anesthesia depth displaying area 81. The visualization parameter information may include at least two parameters representing the depth of anesthesia and the corresponding values, and may be displayed by at least two dimensions in the anesthesia depth displaying area 81. In one embodiment, as shown in FIG. 11, the dimensions could include sedation, analgesia, and muscle relaxation. Each of the three dimensions is indicated by a parameter, such as BIS, $\Delta$HR, and NMT. In addition, the sedation could also be indicated by Minimum Alveolar Concentration (MAC), and the analgesia could also be indicated by $\Delta$BP. Or each dimension may be indicated by two or more parameters, such as the sedation may be indicated by two parameters, $\Delta$BP and $\Delta$HR.

The visualization parameter information could also include graphs corresponding to each dimension, that is, values of the parameters corresponding to each dimension may be visually displayed, such as by rectangular bars. Marks of thresholds for each parameter, such as one or two lines, may be further included in the graphs. Whether parameter values fall within the corresponding threshold may be indicated by colors, patterns, or a combination thereof in the graphs such that a rectangular bar is colored red to attract the attention of the medical staff if the corresponding parameter value does not fall within a threshold range thereof, and the rectangular bar is colored green if the corresponding parameter value falls within the threshold range thereof. The medical staff could quickly view the information displayed in the anesthesia depth displaying area 81, determine the depth of anesthesia, and then quickly decide whether any action should be taken. In one embodiment, each dimension is represented by a shape or chart, such as a rectangular bar, and all shapes or charts are distributed symmetrically around a center point. Information of each dimension is displayed in a centralized manner, so the medical staff could know that the information displayed in the anesthesia depth displaying area 81 is associated and used for indicating the depth of anesthesia. This could enhance the user experience.

The display interface 800 may also include a first setting area 811 and a second setting area 831. The first setting area

811 may be located in the anesthesia depth displaying area 81, and specifically the first setting area 811 may be located below the dimension information. The first setting area 811 may receive dimension information and parameter information corresponding to each dimension, such as a number of dimensions used to indicate the depth of anesthesia, selected dimensions, and parameter information corresponding to each dimension. In some embodiments, in order to avoid incorrect input, the system could just limit the dimension information and/or parameter information inputted by the medical staff to specific ranges. The second setting area 831 may be located in the general parameter displaying area 83. The medical staff could set the display mode or thresholds of parameters displayed in the general parameter displaying area 83 thorough the second setting area 831.

Figure 12:
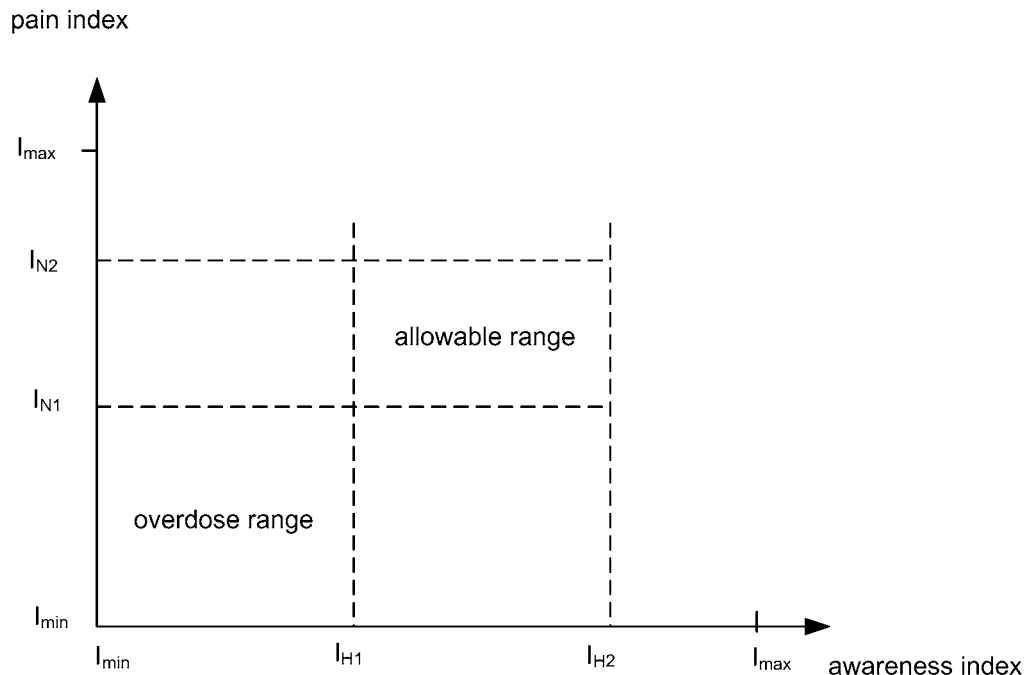
FIG. 12 is a chart of two-dimensional coordinates displaying a depth of anesthesia.

In one embodiment of a method of showing a depth of anesthesia, an awareness index and a pain index are displayed in two-dimensional coordinates, as shown in FIG. 12. A horizontal axis in the coordinates represents the awareness index and a vertical axis in the coordinates represents the pain index. If a threshold range for the awareness index, for example from $I_{H1}$ to $I_{H2}$, and a threshold range for the pain index, for example from $I_{N1}$ to $I_{N2}$, are given, the coordinates may be divided into several regions. At the same time, if an awareness index value of a patient falls within the threshold range of the awareness index and a pain index value of the patient falls within the threshold range of the pain index, it means the anesthetic given to the patient is suitable; if the awareness index value falls below the threshold range of the awareness index and the pain index value falls below the threshold range of the pain index, it means the anesthetic given to the patient is too much; otherwise, it means the anesthetic given to the patient is not suitable.

Figure 13:
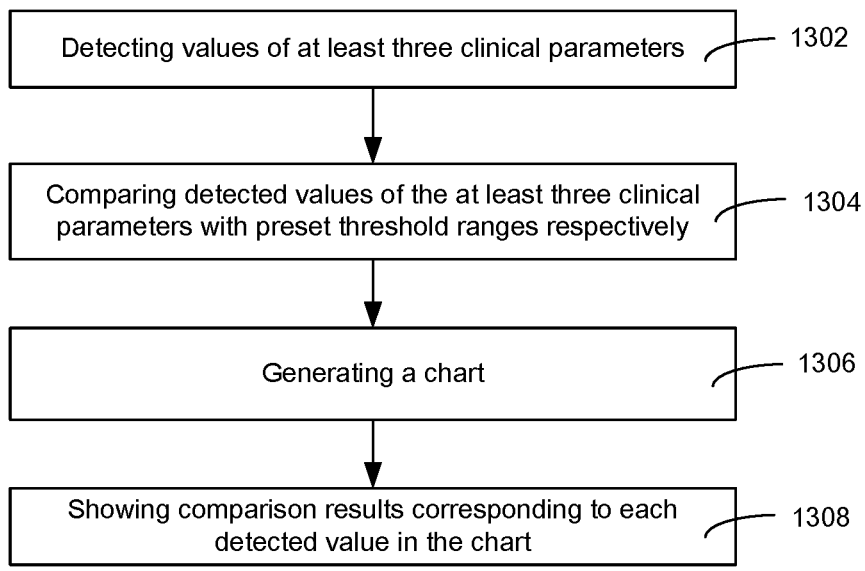
FIG. 13 is a flowchart illustrating a method for displaying clinical parameters according to an embodiment.

As shown in FIG. 13, in one embodiment, a method of displaying clinical parameters includes the following steps.

In Step 1302, values of at least three clinical parameters are detected. Specifically, the values of the at least three clinical parameters may be detected at the same time. A patient's physiological condition, such as depth of anesthesia or atelectasis, may be determined by the values of clinical parameters.

When the method is used to display the depth of anesthesia, the number of detected clinical parameters, which characterize the depth of anesthesia, may be set according to clinical needs, such as three, four, five, and so on. The clinical parameters characterizing the depth of anesthesia may include Bispectral Index (BIS), Train of Four (TOF, also known as neuromuscular monitoring), Minimum Alveolar Concentration (MAC), Systolic (SYS), Heart Rate (HR), Drug Concentration, Index of Hypnosis (also known as consciousness parameter), Index of Nociception (also known as pain index), and so on.

When this method is used to reflect atelectasis, the clinical parameters detected may be at least three hemodynamic parameters, which may be chosen from Saturation of Peripheral Oxygen ($SpO_2$), Pulse Rate (PR), Cardiac Output (CO, units of L/min), Mean Arterial Pressure (MAP), Systolic Blood Pressure (SBP, units of mmHg), Heart Rate (HR, units of beats per minute, bpm), and so on.

In Step 1304, detected values of the at least three clinical parameters are compared with preset threshold ranges, wherein each threshold range corresponds to one clinical parameter.

Figure 14:
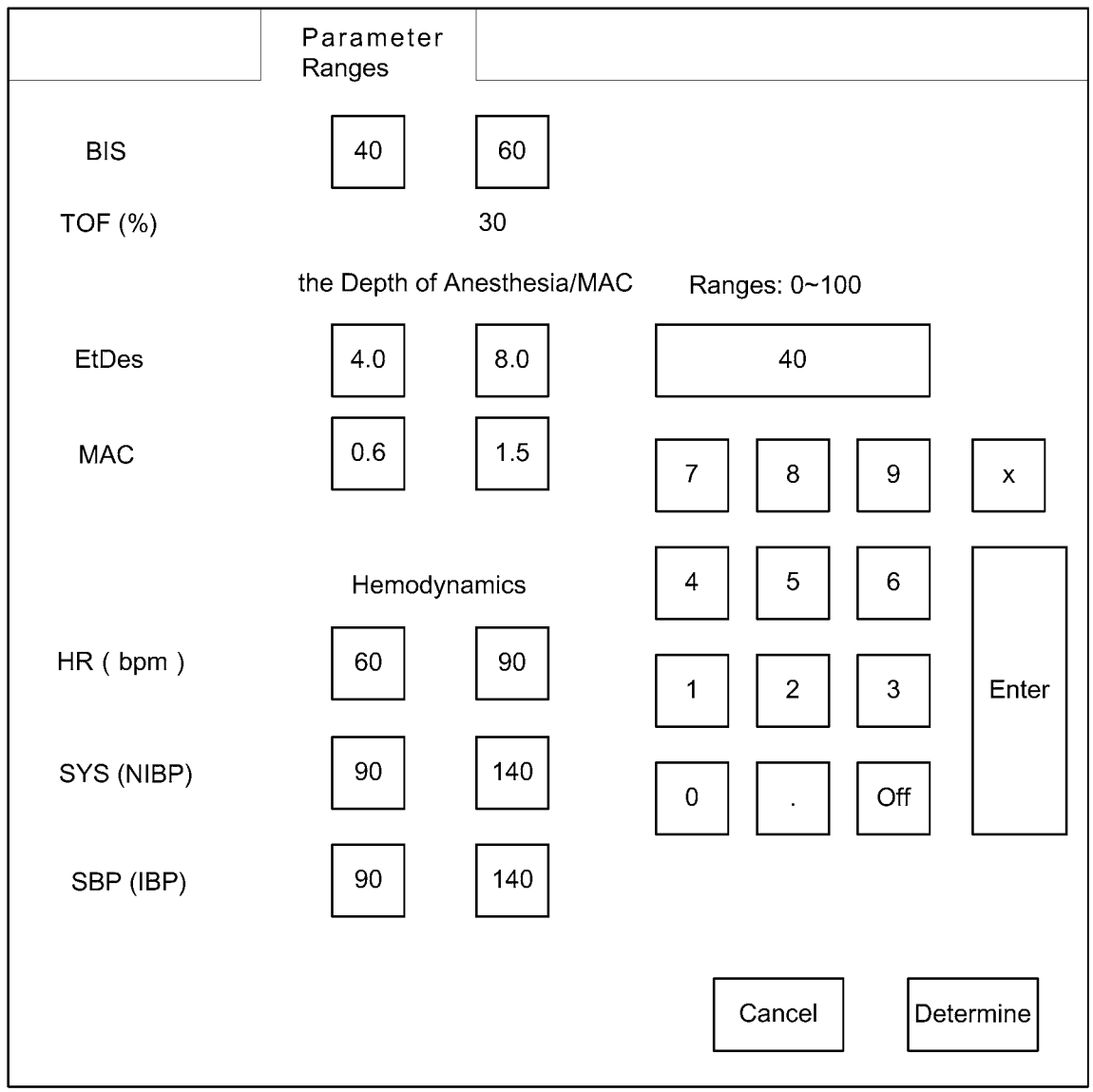
FIG. 14 is a schematic diagram of a user interface for setting threshold ranges of clinical parameters according to an embodiment.

In one embodiment, the threshold ranges corresponding to each clinical parameter are preset. The threshold ranges may be set according to user needs or a default threshold range. FIG. 14 is a schematic diagram of a user interface for setting threshold ranges of clinical parameters. As illustrated, the default threshold of the BIS could range from 40 to 60, the default value of the TOF may be 30, the default threshold of the end-tidal desflurane concentration (EtDes) could range from 4.0 to 8.0, the default threshold of the MAC could range from 0.6 to 1.5, the threshold of the HR in hemodynamics could range from 60 to 90 bmp), the threshold of the PR could range from 60 to 90 bmp, the threshold of the SYS (NIBP) could range from 90 to 140 mmHg, and the threshold of the SYS (IBP) could range from 90 to 140 mmHg. These clinical parameters may be set according to user needs, and the threshold ranges to each clinical parameter may be adjusted as shown below in Table 1.

TABLE 1

| Clinical Parameter | High Limit Value | Low Limit Value | Default Value | Step Size |
|---|---|---|---|---|
| BIS | (low + 2)~100 | 0~(High − 2) | High: 60<br>Low: 40 | 1 |
| TOF | 1, 2, 3, 4,<br>5%~100% | / | High: 30 | 1 |
| EtAA | — | — | / | 0.1 |
| EtDes | (low + 0.2) ~18.0 | 0.0~(high − 0.2) | High: 1.5 times MAC concentration<br>Low: 0.6 times MAC concentration | 0.1 |
| EtIso | (low + 0.2)~5.0 | 0.0~(high − 0.2) | High: 1.5 times MAC concentration<br>Low: 0.6 times MAC concentration | 0.1 |
| EtSev | (low + 0.2)~8.0 | 0.0~(high − 0.2) | High: 1.5 times MAC concentration<br>Low: 0.6 times MAC concentration | 0.1 |
| EtEnf | (low + 0.2)~5.0 | 0.0~(high − 0.2) | High: 1.5 times MAC concentration<br>Low: 0.6 times MAC concentration | 0.1 |
| EtHal | (low + 0.2)~5.0 | 0.0~(high − 0.2) | High: 1.5 times MAC concentration<br>Low: 0.6 times MAC concentration | 0.1 |

TABLE 1-continued

| Clinical Parameter | High Limit Value | Low Limit Value | Default Value | Step Size |
|---|---|---|---|---|
| MAC | low + 0.2)~12.0 | 0.0~high − 0.2) | High: 1.5<br>Low: 0.6 | 0.1 |
| HR | (low + 2)~300 | 15~(high − 2) | High:<br>Adult: 120<br>Children: 160<br>Newborn: 200<br>Low:<br>Adult: 50<br>Children: 75<br>Newborn: 100<br>High Limit Self-learning: an average HR value of 10 minutes before a trachea is inserted +30 | 1 |
| PR | (low + 2)~300 | 15~(high − 2) | the same HR | 1 |
| SYS (NIBP) | Adult:<br>(low + 5)~270 mmHg<br>Children:<br>(low + 5)~200 mmHg<br>Newborn:<br>(low + 5)~135 mmHg | 40~(−5) mmHg | High:<br>Adult: 160<br>Children: 120<br>Newborn: 90<br>Low:<br>Adult: 90<br>Children: 70<br>Newborn: 40 | 1 |
| SYS (IBP) | (low + 2)~300 mmHg | −50~(high − 2) mmHg | the same as SYS (NIBP)<br>High Limit Self-learning: an average SYS value of 10 minutes before a trachea is inserted +30 | 1 |

EtDes represents an end-tidal desflurane concentration; EtIso represents an end-tidal isoflurane concentration; EtSev represents an end-tidal sevoflurane concentration; EtEnf represents an end-tidal enflurane concentration; and EtHal represents an end-tidal halothane concentration.

The detected values of the clinical parameters are compared with the corresponding threshold ranges. For example, the detected value of the BIS is compared with the threshold range of the BIS, which ranges from 40 to 60, then whether the value of the BIS is out of the range, within the range, or below the threshold range may be determined.

In Step 1306, a chart is invoked, wherein the number of variables represented in the chart is decided by the number of the at least three clinical parameters.

Specifically, a chart with three variables is invoked if values of three clinical parameters are detected, a chart with four variables is invoked if values of four clinical parameters are detected, and so on. The chart may show whether each detected value of the clinical parameters is within the corresponding threshold range.

In Step 1308, comparison results corresponding to each detected value may be shown in the chart.

The method of displaying clinical parameters described above detects at least three clinical parameters. The detected values of the clinical parameters are compared with the corresponding threshold ranges, the chart with the corresponding variables is invoked, and then the comparison results corresponding to each detected value may be shown in the chart. Using at least three clinical parameters, the patient's physiological condition may be indicated more accurately during anesthesia or atelectasis. This could help a doctor to quickly and accurately understand the patient's condition, such as the depth of anesthesia, atelectasis, and so on.

In one embodiment, the chart may be a spider chart. Each spoke of the spider chart represents one clinical parameter, and each spoke is divided into three sections. The three sections depict that detected values fall within, above, or below the corresponding threshold ranges.

Figure 15:
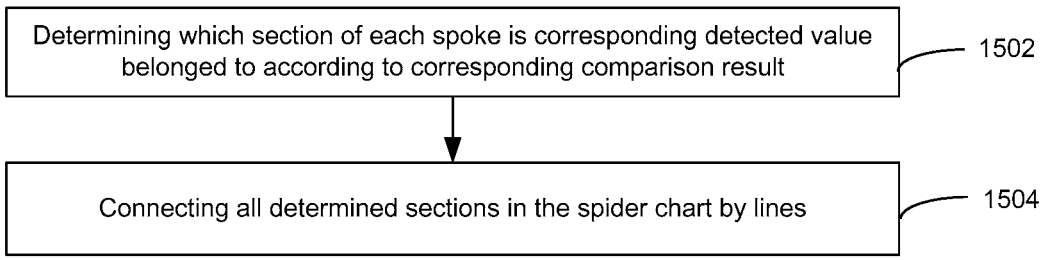
FIG. 15 is a flowchart illustrating how to display comparative results according to an embodiment.

Referring also to FIG. 15, Step 1308 may include the following steps.

In Step 1502, for each spoke, which section a corresponding detected value belongs to may be determined according to the corresponding comparison result.

In Step 1504, all determined sections in the spider chart are connected by lines.

Figure 16A:
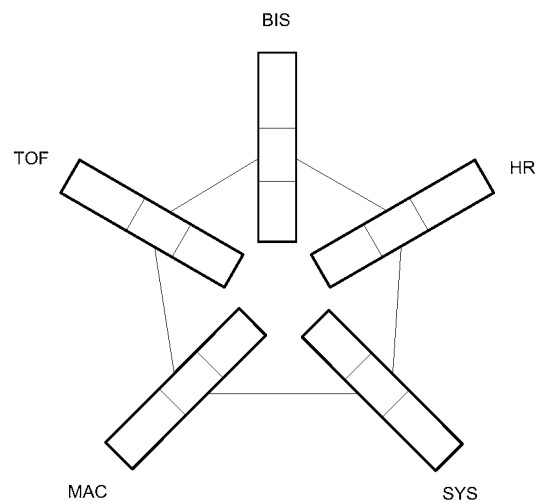
FIG. 16a is a schematic diagram displaying a depth of anesthesia by five clinical parameters according to an embodiment.
Figure 16B:
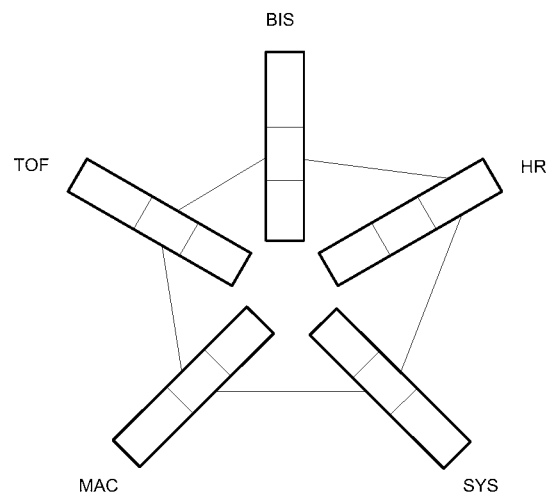
FIG. 16b is a schematic diagram displaying the depth of anesthesia by the five clinical parameters according to another embodiment.
Figure 16C:
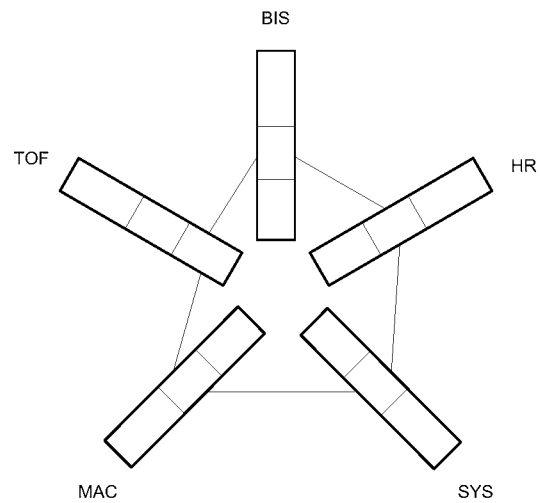
FIG. 16c is a schematic diagram displaying the depth of anesthesia by the five clinical parameters according to another embodiment.

In the following example, the spider chart is used to display the depth of anesthesia, wherein the five clinical parameters may be BIS, TOF, MAC, SYS, and HR. FIG. 16*a* is a schematic diagram displaying the depth of anesthesia, wherein five detected values respectively fall within their threshold ranges; FIG. 16*b* is another schematic diagram displaying the depth of anesthesia, wherein one detected value falls below the corresponding threshold range; and FIG. 16*c* is another schematic diagram displaying the depth of anesthesia, wherein one detected value falls above the corresponding threshold range. As shown in FIGS. 16*a*, 16*b*, and 16*c*, each spoke in the spider chart, displayed as a bar, represents one clinical parameter. Each bar may include three sections: a middle section representing whether a detected value of a corresponding clinical parameter falls within the corresponding threshold range, a section near the center of the spider chart representing whether a detected value of the corresponding clinical parameter falls below the corresponding threshold range, and a section far away from the center of the spider chart representing whether a detected value of the corresponding clinical parameter falls above the corresponding threshold range. A length of each spoke may be fixed, and a length of each section may be fixed. If all detected values fall within the corresponding threshold ranges, the lines connected to all determined sections form an equilateral pentagon, or the lines connected to all determined sections may not form an equilateral pentagon. In addition, in other embodiments, each spoke may be displayed as other shapes, such as an inverted triangle.

Figure 17A:
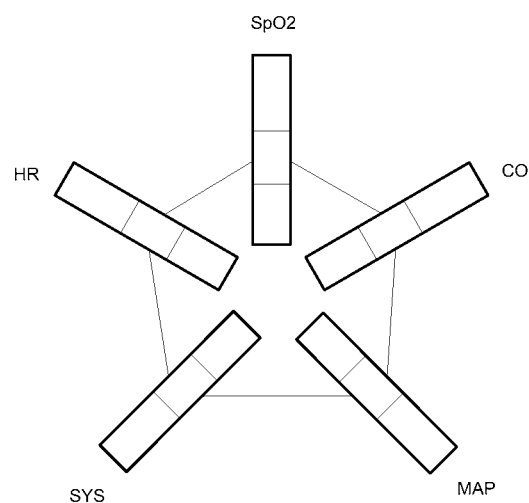
FIG. 17a is a schematic diagram reflecting atelectasis by five clinical parameters according to an embodiment.
Figure 17B:
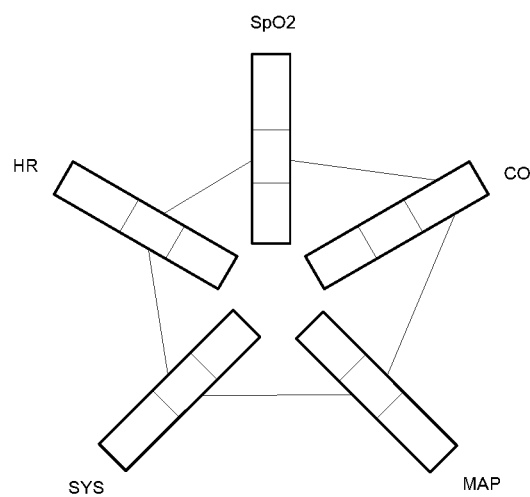
FIG. 17b is a schematic diagram reflecting atelectasis by the five clinical parameters according to another embodiment.
Figure 17C:
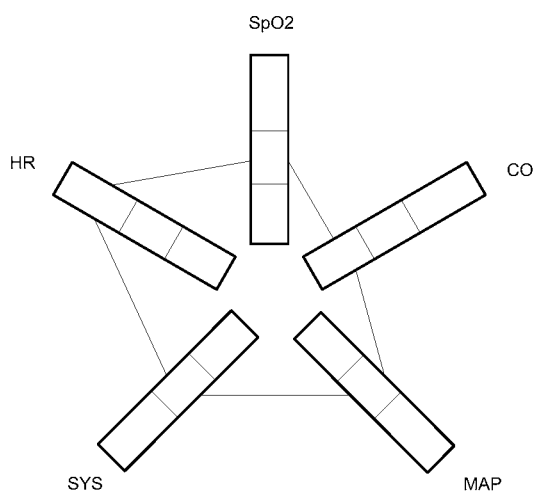
FIG. 17c is a schematic diagram reflecting atelectasis by the five clinical parameters according to another embodiment.

In the following example, the spider chart is used to display atelectasis, wherein the five clinical parameters may comprise $SpO_2$, CO, MAP, SBP, and HR. FIG. 17a is a schematic diagram reflecting atelectasis, wherein five detected values of the clinical parameters respectively fall within the corresponding threshold ranges; FIG. 17b is another schematic diagram reflecting atelectasis, wherein the detected CO value falls below the corresponding CO threshold range; and FIG. 17c is another schematic diagram reflecting atelectasis, wherein the detected HR value falls above the corresponding HR threshold range and the detected CO value falls below the corresponding CO threshold range.

Thereafter, the detected values of the at least three clinical parameters are displayed in the chart.

Figure 18A:
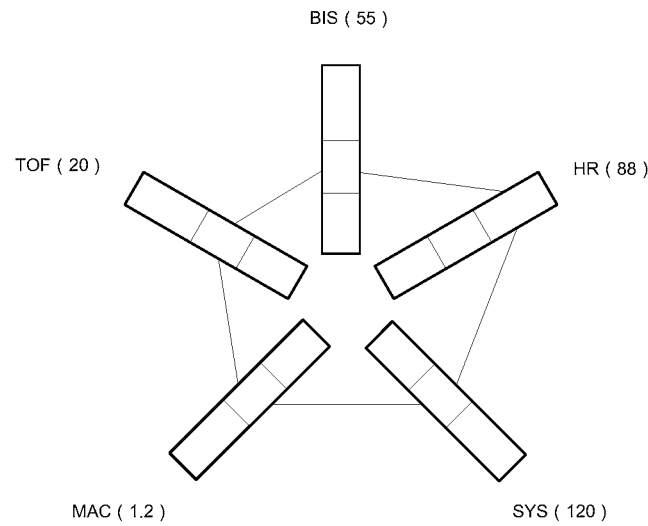
FIG. 18a is a schematic diagram displaying the depth of anesthesia according to another embodiment.
Figure 18B:
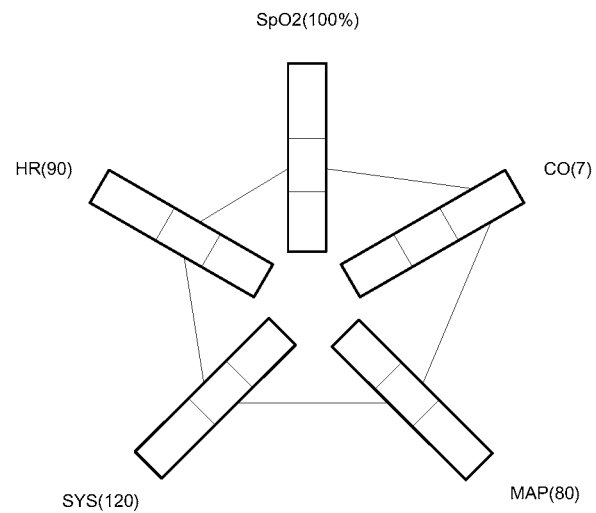
FIG. 18b is a schematic diagram reflecting atelectasis according to another embodiment.

In one embodiment, as shown in FIG. 18a, the depth of anesthesia is shown in the chart, wherein the clinical parameters may include BIS (the value of the BIS is 55), TOF (the value of the TOF is 20), HR (the value of the HR is 88), MAC (the value of the MAC is 1.2), and SYS (the value of the SYS is 120).

The number and kinds of the at least three clinical parameters may be preset in some embodiments. For example, the method is used to display the depth of anesthesia, if four clinical parameters are used to reflect the depth of anesthesia, the number of the at least three clinical parameters, which is four, may be set and the kinds of the at least three clinical parameters may be selected on corresponding configuration interfaces.

In another embodiment, after Step 1504, the method may continue as follows:

each determined section may be colored according to the corresponding comparison result; and/or the lines may be colored according to the comparison results.

For example, if a detected value of a clinical parameter does not fall within the corresponding threshold range, the section that the detected value of the clinical parameter belongs to is colored yellow; if the detected value of the clinical parameter falls within the corresponding threshold range, the section that the detected value of the clinical parameter belongs to is colored red.

In one embodiment, the step of coloring the lines according to the comparison results may be the lines are colored according to a number of the detected values that do not fall within the corresponding threshold ranges.

Specifically, a relationship between colors of the lines and the comparison results may be preset. For example, if all detected values of the clinical parameters fall within the corresponding threshold ranges, the lines are colored green (indicating that the number of the detected values that do not fall within the corresponding threshold is 0); if one of the detected values of the clinical parameters does not fall within the corresponding threshold range, the lines are colored yellow (that means the number of detected values that do not fall within the corresponding threshold ranges is 1); if at least two detected values of the clinical parameters do not fall within the corresponding threshold ranges, the lines are colored red (that means the number of detected values of the clinical parameters that do not fall within the corresponding threshold ranges is 2 or larger than 2), and sections corresponding to the clinical parameter values that do not fall within the corresponding threshold ranges are marked by red. This is an example, and one skilled in the art could know other ways that may be used to color the lines or sections.

In one embodiment, the chart is a spider chart, and each spoke is divided into three sections.

Figure 19:
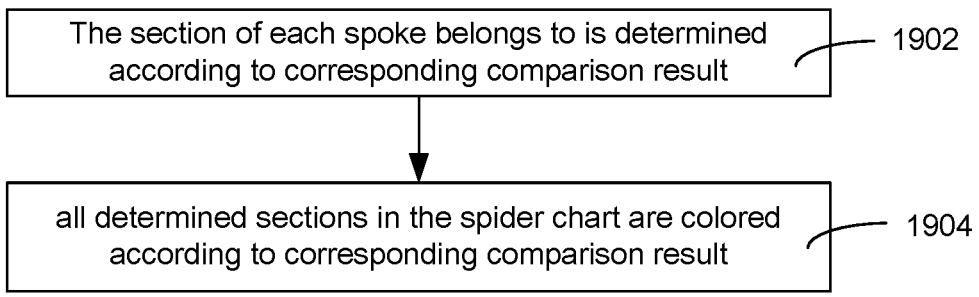
FIG. 19 is a flowchart illustrating how to display comparative results according to another embodiment.

Referring also to FIG. 19, Step 1308 may include the following steps:

In Step 1902, for each spoke in the spider chart, which section a corresponding detected value belongs to may be determined according to the corresponding comparison result;

In Step 1904, all determined sections in the spider chart are colored according to the corresponding comparison result.

By coloring the sections that the corresponding detected values belong to, the spider chart could reflect the depth of anesthesia and atelectasis directly, making it easy for the doctor to make a decision quickly.

In one embodiment, the chart may be a combination chart with multiple independent diagrams, and each diagram represents one clinical parameter. In this embodiment, the chart may include multiple bar graphs.

Colors and/or detected values of the at least three clinical parameters may be displayed in the chart according to the comparison results.

In addition, for each bar graph showing the value of one clinical parameter, a fixed or variable scale may be set, and corresponding threshold ranges may be displayed.

Figure 20A:
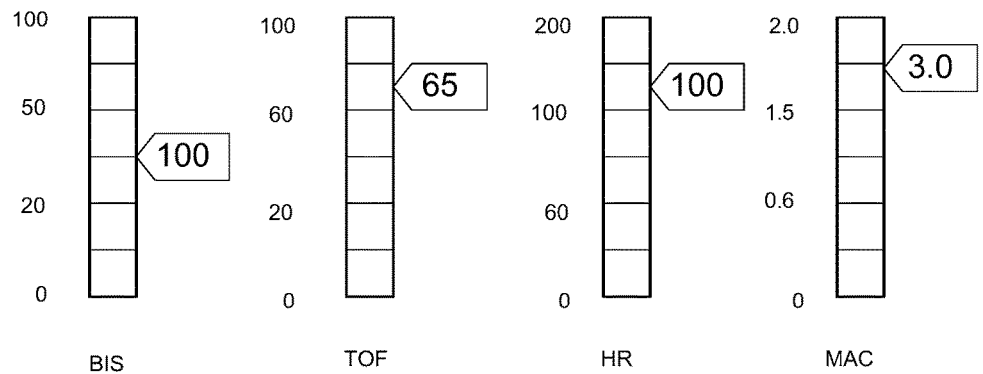
FIG. 20a is a schematic diagram displaying the depth of anesthesia by bar graphs according to another embodiment.

As shown in FIG. 20a, the depth of anesthesia is displayed by bar graphs. In this example, the detected value of the BIS is 100, the detected value of the TOF is 65, the detected value of the HR is 100, and the detected value of the MAC is 3.0.

Figure 20B:
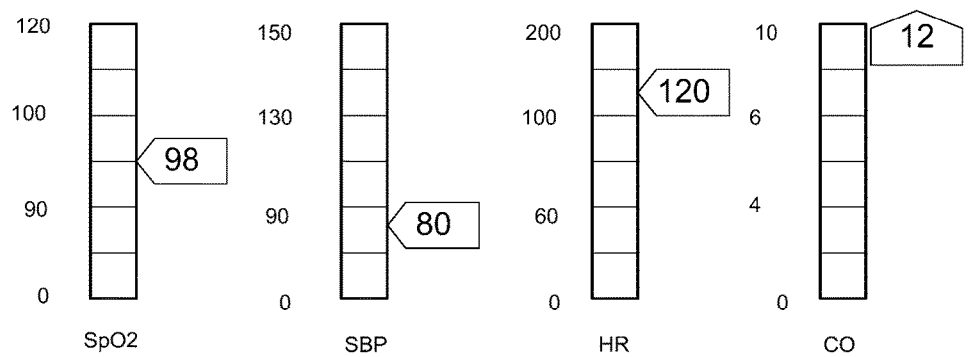
FIG. 20b is a schematic diagram reflecting atelectasis by bar graphs according to another embodiment.

As shown in FIG. 20b, atelectasis may be reflected by bar graphs. In this example, the detected value of the $SpO_2$ is 98, the detected value of the SBP is 80, the detected value of the HR is 120 bmp, and the detected value of the CO is 12 L/min.

Figure 21:
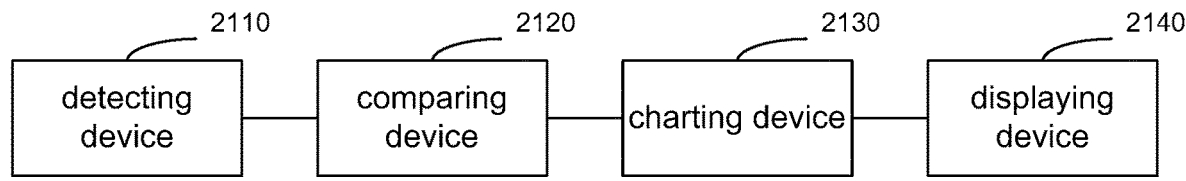
FIG. 21 is a schematic diagram of a system for displaying clinical parameters according to another embodiment.

A system for displaying clinical parameters is shown in FIG. 21. The system includes a detecting device 2110, a comparing device 2120, an charting device 2130, and a display device 2140.

The detecting device 2110, including sensors, could detect values of at least three clinical parameters.

The system in this embodiment may be used to indicate the physiological status of the patient, for example, the system is used to indicate the depth of anesthesia, atelectasis, and so on. If the system is used to indicate the depth of anesthesia, the clinical parameters to be detected may be clinical signs and/or drug concentration, and the number of the clinical parameters to be detected, such as three, four, or five, may be set according to need. In this embodiment, the clinical parameters used to indicate the depth of anesthesia may be selected from BIS, MAC, SYS, HR, Drug Concentration, Index of Hypnosis, Index of Nociception, and so on. The detecting device 2110 could include different types of sensors, and each type of sensor detects one clinical parameter; or the detecting device 2110 could include one type of sensors, and the sensors could detect all the clinical parameters.

If the system is used to indicate atelectasis, the clinical parameters to be detected may be hemodynamic parameters. The at least three clinical parameters could selected from SpO$_2$, PR, CO (units of L/min), MAP, SBP (units of mmHg), HR (units of beats per minute, bpm), and so on.

In addition, the detecting device 2110 could detect values of the at least three clinical parameters at the same time.

The comparing device 2120 compares detected values of the at least three clinical parameters with preset threshold ranges, wherein each threshold range corresponds to one clinical parameter.

Specifically, the threshold ranges corresponding to each clinical parameter may be preset according to need or by default threshold ranges. The detected values of the clinical parameters are compared with the corresponding threshold ranges; for example, the detected value of BIS is compared with a threshold range of BIS, which ranges from 40 to 60, and then whether the detected value falls within, above, or below the threshold range is determined.

The charting device 2130 generates a chart, wherein the number of variables represented in the chart is decided by the number of the at least three clinical parameters.

Specifically, the charting device 2130 generates a chart with three variables if values of three clinical parameters are detected, and the charting device 1130 generates a chart with four variables if values of four clinical parameters are detected. The chart may show whether each detected value of the clinical parameters is within the corresponding threshold range.

The display device 2140 displays comparison results corresponding to each detected value in the chart.

In the method or system for displaying clinical parameters, values of at least three clinical parameters are detected, detected values of the clinical parameters are compared with the corresponding threshold ranges, and then a chart with the corresponding number of variables is invoked to display the comparison results. Using at least three clinical parameters, the patient's physiological condition may be indicated more accurately during anesthesia or atelectasis. This could help the doctor to quickly and accurately understand the patient's condition, such as the depth of anesthesia, atelectasis, and so on.

In one embodiment, the chart is a spider chart. Each spoke of the spider chart represents one clinical parameter, and each spoke is divided into three sections.

For each spoke, the display device 2140 could determine which section a corresponding detected value belongs to according to the corresponding comparison result, and then the display device 2140 connects all determined sections in the spider chart by lines.

The lines connecting the determined sections could form a shape, and the depth of anesthesia may be directly and accurately indicted by the shape.

In addition, the display device 2140 could color the determined sections and/or the lines according to the corresponding comparison results in the chart.

Specifically, a relationship between colors of the lines and the comparison results may be preset. For example, if all detected values of the clinical parameters fall within the corresponding threshold ranges, the lines are colored green (that means the number of the detected values that do not fall within the corresponding threshold ranges is 0); if one of the detected values of the clinical parameters does not fall within the corresponding threshold range, the lines are colored yellow (that means the number of detected values that do not fall within the corresponding threshold ranges is 1); if at least two detected values of the clinical parameters do not fall within the corresponding threshold ranges, the lines are colored red (that means the number of detected values of the clinical parameters that do not fall within the corresponding threshold ranges is 2 or larger than 2), and sections corresponding to the clinical parameter values that do not fall within the corresponding threshold ranges are marked by red. This is an example, and one skilled in the art could know other ways that may be used to color the lines or sections.

In another embodiment, the chart is a spider chart, and each spoke is divided into three sections.

For each spoke, the display device 2140 could determine which section a corresponding detected value belongs to and color the determined section according to the corresponding comparison result. By coloring the determined sections that the detected values belong to, the depth of anesthesia may be indicated directly, making it is easy for the doctor to make a decision quickly.

In addition, the display device 2140 could further display the detected values of the clinical parameters in the chart.

In another embodiment, the chart may be a combination chart with multiple independent diagrams, and each diagram represents one clinical parameter. The display device 2140 could color the determined sections and/or display the detected values of the clinical parameters in the combination chart.

Even though the patient monitoring systems or other medical devices discussed above may indicate the depth of anesthesia, one skilled in the art could know the systems or devices could also indicate other kinds of information if the information of each dimension and corresponding parameters are replaced with other appropriate information.

The systems discussed herein may be implemented by known devices, such as general computers, computer programming tools, digital storage media, and computer networks. The computers could include microprocessors, microcontrollers, logic circuits, and other processing units, and the processing units could include dedicated processors, such as Application Specific Integrated Circuit (ASIC), Programmable Array Logic (PAL), Programmable Logic Array (PLA), Programmable Logic Device (PLD), and Field Programmable Gate Array (FPGA). The computers could also include a readable storage medium, such as a non-transitory storage medium, a static RAM, a dynamic RAM, a ROM, a CD-ROM, a disk, a tape, and a magnetic/optical/flash memory card.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, advantages, and solutions to problems have been described above with regard to various embodiments and are not to be construed as critical, required, or essential features or elements. The scope of the present disclosure should, therefore, be determined by the following claims.

What is claimed is:

1. A computer display system to display clinical parameters, the system comprising:
   a parameter acquiring device configured to receive at least three clinical parameters of a patient at a particular time; and
   a processing unit in communication with the parameter acquiring device and a display device, wherein,
the processing unit is configured to receive the at least three clinical parameters and cause the display device to display a spider chart based on the at least three clinical parameters,
the spider chart includes a plurality of radial spokes,
each spoke of the plurality of radial spokes represents a range of values for a respective one of the at least three clinical parameters and indicating (i) a point corresponding to a detected value of the respective one of the at least three clinical parameters, and (ii) a threshold range of the respective one of the at least three clinical parameters,
the threshold range includes an upper limit spaced from a lower limit along a respective one of the plurality of radial spokes, the lower limit and the upper limit are spaced from a beginning point of the range and an end point of the range along the respective one of the plurality of radial spokes,
the threshold range for at least one of the at least three clinical parameters is preset, and,
the processing unit is configured to display each spoke of the plurality of radial spokes as a rectangular bar with an inner section displayed closest to a center of a spider graph representing a first range of values below the threshold range, a middle section representing a second range of values within the threshold range, and an outer section displayed furthest from the center of the spider graph representing a third range of values above the threshold range.

2. The system of claim 1, wherein the processing unit is configured to visually connect the point corresponding to the detected value for each of the plurality of radial spokes together.

3. The system of claim 1, wherein the processing unit is configured to draw lines between points corresponding to detected values on adjacent spokes.

4. The system of claim 1, wherein the point is defined above, below, or within the threshold range.

5. The system of claim 1, wherein the at least three clinical parameters are selected from the group consisting of bispectral Index (BIS), train of four (TOF), minimum alveolar concentration (MAC), neuromuscular transmission (NMT), systolic blood pressure (SYS), heart rate (HR), drug concentration, index of hypnosis, index of nociception, saturation of peripheral oxygen ($SpO_2$), pulse rate (PR), cardiac output (CO), and mean arterial pressure (MAP).

6. The system of claim 1, wherein the spider chart represents a depth of anesthesia and includes spokes corresponding to the clinical parameters for bispectral Index (BIS), train of four (TOF), minimum alveolar concentration (MAC), neuromuscular transmission (NMT), systolic blood pressure (SYS), and heart rate (HR).

7. A computerized method to display clinical parameters, the method comprising
detecting, via a plurality of sensors, values of at least three clinical parameters of a patient at a particular time; and
processing, via a processing unit, the at least three clinical parameters and causing a display device to display a spider chart based on the at least three clinical parameters,
wherein,
the spider chart includes a plurality of radial spokes,
each spoke of the plurality of radial spokes represent a range of values for a respective one of the at least three clinical parameters and indicating (i) a point corresponding to a detected value of the respective one of the at least three clinical parameters, and (ii) a threshold range of the respective one of the at least three clinical parameters,
the threshold range has an upper limit spaced from a lower limit along a respective one of the plurality of radial spokes,
the lower limit and the upper limit are spaced from a beginning point of the range and an end point of the range along the respective one of the plurality of radial spokes
the threshold range for at least one of the at least three clinical parameters is preset, and
the processing unit is configured to display each spoke of the plurality of radial spokes as a rectangular bar with an inner section displayed closest to a center of a spider graph representing a first range of values below the threshold range, a middle section representing a second range of values within the threshold range, and an outer section displayed furthest from the center of the spider graph representing a third range of values above the threshold range.

8. A computer system for graphically representing a depth of anesthesia for a patient, the system comprising:
a parameter acquiring device configured to detect, via a plurality of sensors, at least two sets of clinical parameters for the patient at a particular time; and
a processing device in communication with the parameter acquiring device and a display device,
wherein,
the processing device is configured to receive the at least two sets of clinical parameters and cause the display device to display graphical representations of the at least two sets of clinical parameters in at least two respective areas of the display device,
the at least two sets of clinical parameters are selected from a group consisting of muscle relaxation, awareness, and pain strength,
one of the graphical representations includes a threshold of one of the at least two sets of clinical parameters,
another of the graphical representations includes a threshold range of another of the at least two sets of clinical parameters,
the threshold range has a beginning point and an end point,
the threshold range is preset, and
the processing device is configured to display the another of the graphical representations as a rectangular bar with an inner section displayed closest to a center of a spider graph representing a first range of values below the threshold range, a middle section representing a second range of values within the threshold range, and an outer section displayed furthest from the center of the spider graph representing a third range of values above the threshold range.

9. The system of claim 8, wherein both of the graphical representations include a graph.

10. The system of claim 8, wherein one of the at least two sets of clinical parameters represents pain strength.

11. The system of claim 8, wherein the at least two sets of clinical parameters include change in blood pressure and change in heart rate.

12. The system of claim 8, wherein one of the at least two sets of clinical parameters is the muscle relaxation and indicates neuromuscular transmission (NMT).

13. The system of claim 8, wherein one of the at least two sets of clinical parameters is the awareness and indicates a bispectral Index (BIS).

14. The system of claim 8, wherein the graphical representations are arranged as a spider chart.

15. A computerized method for graphically representing a depth of anesthesia for a patient, the method comprising:

detecting, via a plurality of sensors, at least two sets of clinical parameters for the patient at a particular time; and processing, via a processing unit, the at least two sets of clinical parameters and causing a display device to display graphical representations of the at least two sets of clinical parameters in at least two respective areas of the display device, wherein, the at least two sets of clinical parameters are selected from a group consisting of muscle relaxation, awareness, and pain strength, one of the graphical representations includes a threshold of one of the at least two sets of clinical parameters, another of the graphical representations includes a threshold range of another of the at least two sets of clinical parameters, the threshold range has a beginning point and an end point, the threshold range is preset, and the processing unit is configured to display the another of the graphical representations as a rectangular bar with an inner section displayed closest to a center of a spider graph representing a first range of values below the threshold range, a middle section representing a second range of values within the threshold range, and an outer section displayed furthest from the center of the spider graph representing a third range of values above the threshold range.

* * * * *